United States Patent [19]

Shroff et al.

[11] 4,329,345
[45] May 11, 1982

[54] N-(-2-PYRIMIDINYL)-4-ARYL-4-[N'-(ALKYLAMINO ALKYL)]-PIPERIDINAMIDE

[75] Inventors: James R. Shroff, Riverside, Conn.; Rohit Desai, Yonkers, N.Y.

[73] Assignee: USV Pharmaceutical Corporation, Tuckahoe, N.Y.

[21] Appl. No.: 144,469

[22] Filed: Apr. 28, 1980

[51] Int. Cl.³ .................. C07D 211/28; A61K 31/44
[52] U.S. Cl. .................................. 424/251; 544/332; 544/320; 544/122; 546/206; 546/207
[58] Field of Search ............... 544/332, 122, 320; 546/206, 207; 424/251

[56] References Cited
U.S. PATENT DOCUMENTS 3,259,623  7/1966  Kober et al. ................. 544/330
3,334,106  8/1967  Biel .............................. 544/122
4,157,393  6/1979  Sanczuk et al. ............. 544/332

*Primary Examiner*—Anton H. Sutto
*Assistant Examiner*—Sharon A. Gibson

[57] ABSTRACT

Compounds of the formula

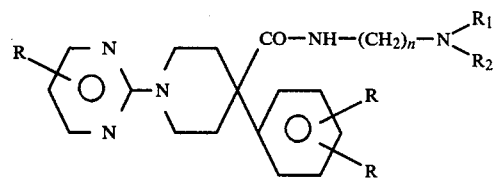

wherein
R is hydrogen, alkyl, alkoxy, halo, amino, alkylamino, dialkylamino, hydroxy, nitro, trifluoromethyl, mercapto, or alkylmercapto, and may be the same or different,
n is an integer from 2 to 4, and
$R_1$ and $R_2$ are hydrogen or alkyl and may be the same or different, or $R_1$ and $R_2$ taken together with the nitrogen to which they are attached may be pyrrolidino, piperidino or morpholino and their pharmaceutically acceptable, non-toxic acid addition salts have anti-arrhythmic activity.

5 Claims, No Drawings

N-(-2-PYRIMIDINYL)-4-ARYL-4-[N'-(AL-KYLAMINO ALKYL)]-PIPERIDINAMIDE

This invention relates to new organic compounds having valuable pharmacological activity. In particular the invention relates to piperidyl pyrimidines of the formula

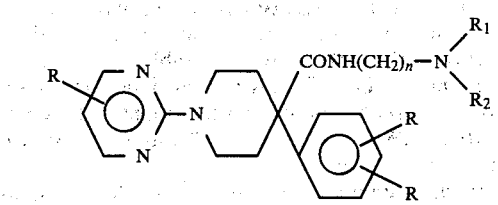

and their pharmaceutically acceptable, non-toxic acid addition salts, wherein

R is hydrogen, alkyl, alkoxy, halo, amino, alkylamino, dialkylamino, hydroxy, nitro, trifluoromethyl, mercapto, or alkylmercapto, and may be the same or different. $R_1$ and $R_2$ are hydrogen or alkyl and may be the same or different or $R_1$ and $R_2$ taken together with the nitrogen to which they are attached may be pyrrolidino, piperidino or morpholino, and n is an integer from 2 to 4 inclusive.

The alkyl groups in R, $R_1$ and $R_2$, and in the R alkoxy alkylmercapto, alkylamino, and dialkylamino groups are preferably lower alkyl groups which may be branched or straight chained and contain from 1 to 6 carbon atoms. These groups include methyl, ethyl, propyl, isopropyl, butyl, sec-butyl, isobutyl, amyl, isoamyl, hexyl and the like.

The halo groups may be fluoro, chloro, bromo or iodo.

There may be more than one R substituent on the benzene ring and when there are more than one, they may be the same or different.

The compounds of the present invention were obtained by the following reaction scheme:

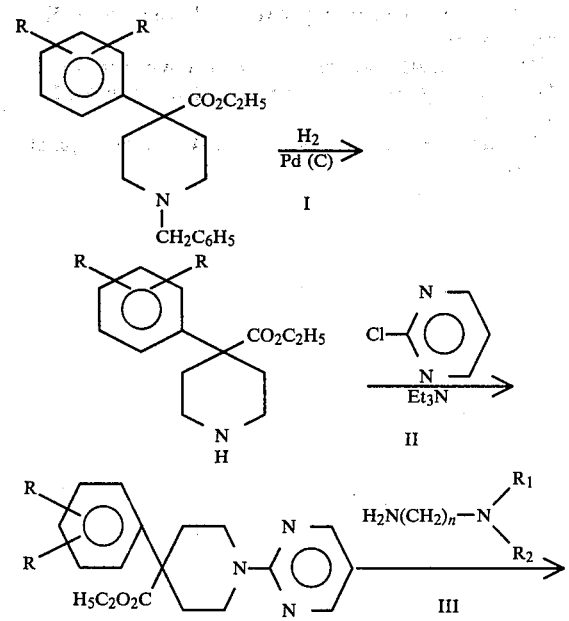

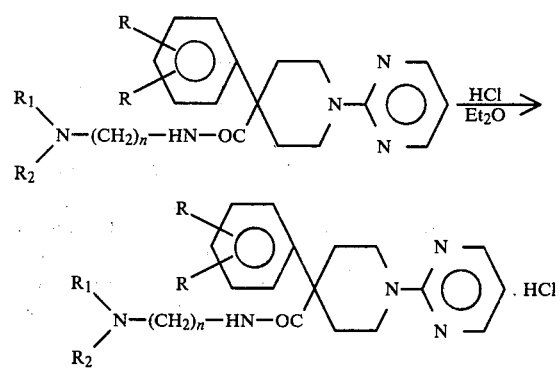

-continued wherein R, $R_1$, $R_2$ and n are the same as above.

In the above sequence the hydrochloride salts were obtained by the reaction of the free base with hydrogen chloride in ether. The same method can be used for the preparation of other acid addition salts. Suitable acids for the preparation of such salts include hydrobromic, phosphoric, sulfuric, benzoic, mandelic, cinnamic, acetic, maleic, fumaric, malonic, malic, succinic, and the like.

The steps in the above sequence may, if desired, be changed. For example, step III, the reaction of the ester with the amine

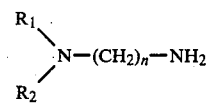

may precede step I, the reductive cleavage of the benzyl group.

The invention will be more fully illustrated in the examples that follow. These examples are given by way of illustration and are not to be considered as limiting.

EXAMPLE I

N-(2-Pyrimidinyl)-4-phenyl-4-carboethoxy piperidine

To a mixture of 4.0 gms (0.017 mole) 4-phenyl-4-carboethoxy-piperidine and 1.72 gms (0.017 mole) of triethylamine in 50 ml. toluene was added dropwise 2.0 gms (0.017 mole) 2-chloropyrimidine. Triethylamine hydrochloride started to precipitate out almost immediately. The reaction mixture was warmed to 70°–80° for a period of two hours, and then allowed to cool. The triethylamine hydrochloride was filtered off and the filtrate washed with water (to remove the last traces of triethylamine hydrochloride). The residue was recrystallized from acetone to yield 2.5 gms (47% yield), m.p. 119°–120°.

EXAMPLE II

N-(2-Pyrimidinyl)-4-phenyl-4-[N'-(2-diethylaminoethyl)]piperidinamide hydrochloride monohydrate N-Benzyl-4-phenyl-4-[N'-(2-diethylaminoethyl)]-piperidinamide A mixture of 12 gms (0.037 mole) N-benzyl-4-phenyl-4-carboethoxypiperidine and 20 gms (0.17 mole) diethylaminoethylamine was heated in a bomb, bath temperature maintained around 150° C. The reaction mixture was heated for a period of 2 days and allowed to cool. The solid material (8.5 gms) obtained after filtration was washed with a small quantity of isopropanol and dried.

EXAMPLE III

N-(2-Pyrimidinyl)-4-phenyl-4-[N'-(2-diethylaminoethyl)]piperidinamide (A) 8.5 gms (0.021 mole) of the crude N-benzyl-4-phenyl-4-[N'-(2-diethyalminoethyl)]-piperidinamide was dissolved in 200 ml methanol and hydrogenated catalytically (0.5 gms. 10% Pd/Carbon). A total of 15 #$H_2$ was absorbed over a period of a few hours. The palladium on carbon was filtered off, the solvent removed from the filtrate to obtain 6.4 gms of oily material.

(B) 6.4 gms (0.021 mole) of 4-phenyl-4-[N-2(2-diethylaminoethyl)]piperidinamide, 2.4 gms (0.021 mole) 2-chloropyrimidine and 2.1 gms (0.021 mole) of triethylamine were dissolved in 50 ml toluene and the reaction mixture refluxed for a period of 4–6 hours. The triethylamine hydrochloride was filtered off, the solvent removed from the filtrate and the residue treated with ethereal hydrogen chloride to form the hydrochloric salt. Recrystallization from ethanol yielded 4.5 gms (50% yield) melting at 223°–25° C.

By following the procedures in the above examples the following additional compounds were prepared:

| R | n | $-NR_1R_2$ |
|---|---|---|
| H | 3 | $-N(C_2H_5)_2$ |
| H | 2 | $-N(CH_3)_2$ |
| H | 2 | $-N(C_2H_5)_2$ |
| H | 2 |  |
| H | 4 | $-N(C_2H_5)_2$ |
| H | 2 | $-NHC_2H_5$ |
| 4-Cl | 2 | $-N(C_2H_5)_2$ |
| 4-Br | 2 | $-N(C_2H_5)_2$ |
| 4-$NH_2$ | 2 | $-N(C_2H_5)_2$ |
| 4-$N(C_2H_5)_2$ | 2 | $-N(C_2H_5)_2$ |
| 4-OH | 3 | $-N(C_2H_5)_2$ |
| 4-$H_3CO$ | 2 | $-N(CH_3)_2$ |
| 2-$NO_2$ | 4 | $-N(C_2H_5)_2$ |
| H | 2 | $-N(CH_3)C_2H_5$ |
| 4-$CF_3$ | 2 | $-N(C_2H_5)_2$ |
| 4-SH | 2 | $-N(C_2H_5)_2$ |
| 2-Cl—4-$CH_3$ | 2 | $-N(C_2H_5)_2$ |
| 2,4-di-$CH_3$ | 2 | $-N(C_2H_5)_2$ |
| 4-$C_2H_5$ | 2 | $-N(C_2H_5)_2$ |
| 4-i-$C_3H_7$ | 2 | $-N(C_2H_5)_2$ |
| 4-F | 2 | 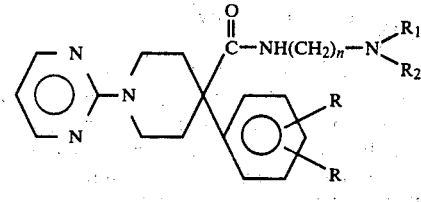 | exhibited an $ED_{50}$ at a concentration of about 3.2 mg/l.

In in vivo screening against chloroform induced ventricular arrhythmia mice, the compounds exhibited an $ED_{50}$ of about 10 mg/kg. This will enable a physician to select the proper dose for his patient depending upon age, weight, sex and other considerations. The compound wherein R is hydrogen, n is 2 and $R_1$ and $R_2$ are ethyl is the most active.

The compounds may be mixed with solid or liquid pharmaceutical carriers and formulated into tablets, powders, or capsules for oral administration or dissolved in suitable solvents for either oral or parenteral administration.

We claim:

1. A compound having anti-arrhythmic activity selected from the group consisting of compounds of the formula

wherein
R is H or alkyl group having 1 to 6 carbon atoms,
n is an integer from 2 to 4 and
$R_1$ and $R_2$ are hydrogen or alkyl having 1 to 6 carbon atoms and may be the same or different, or
$R_1$ and $R_2$ taken together with the nitrogen to which they are attached may be pyrrolidino, piperidino, or morpholino and
their pharmaceutically acceptable, nontoxic acid addition salts.

2. A compound according to claim 1 wherein the R's are hydrogen.

3. A compound according to claim 1 wherein n is 2.

4. A compound according to claim 3 wherein the R's are hydrogen.

5. A compound according to claim 4 wherein $R_1$ and $R_2$ are ethyl.

* * * * *